(12) United States Patent
Ueno et al.

(10) Patent No.: US 6,673,962 B2
(45) Date of Patent: Jan. 6, 2004

(54) GRANULE OF PARAHYDROXYBENZOIC ACID OR PARAHYDROXYBENZOIC ESTER AND PROCESS FOR PRODUCING THE SAME

(75) Inventors: Ryuzo Ueno, Nishinomiya (JP); Masaya Kitayama, Takarazuka (JP); Nobutaka Izumichi, Ashiya (JP); Masaharu Kittaka, Takarazuka (JP)

(73) Assignee: Kabushiki Kaisha Ueno Seiyaku Oyo Kenkyujo, Osaka (JP)

( * ) Notice: Subject to any disclaimer, the term of this patent is extended or adjusted under 35 U.S.C. 154(b) by 0 days.

(21) Appl. No.: 10/311,633

(22) PCT Filed: Apr. 18, 2002

(86) PCT No.: PCT/JP02/03851

§ 371 (c)(1),
(2), (4) Date: Dec. 18, 2002

(87) PCT Pub. No.: WO02/085835

PCT Pub. Date: Oct. 31, 2002

(65) Prior Publication Data

US 2003/0160205 A1 Aug. 28, 2003

(30) Foreign Application Priority Data

Apr. 20, 2001 (JP) ........................................ 2001-122933

(51) Int. Cl.[7] ............................................... C07C 65/01
(52) U.S. Cl. ...................................................... 562/475
(58) Field of Search .......................................... 562/475

(56) References Cited

FOREIGN PATENT DOCUMENTS

| JP | 56-155714 A | | 12/1981 |
|---|---|---|---|
| JP | 59-196841 | * | 11/1984 |
| JP | 61212533 | * | 9/1986 |
| JP | 5-293357 A | | 11/1993 |
| JP | 6-285355 A | | 10/1994 |

OTHER PUBLICATIONS

12996 Chemical Commodities, The Chemical Daily Co., Ltd., 1996, ISBN 4–87326–204–6, pp. 581, 1287 and 1288.

* cited by examiner

*Primary Examiner*—Alan L. Rotman
*Assistant Examiner*—Hector M. Reys
(74) *Attorney, Agent, or Firm*—Sughrue Mion, PLLC

(57) ABSTRACT

Granular product of parahydroxybenzoic acid or its ester which exhibits well suppressed dusting and caking tendency and a process for preparing the product are provided. The granular product of parahydroxybenzoic acid or its ester according to the instant invention has an average particle size of equal to or more than 150 $\mu$m and a hardness of 10–3000 g. The granular product of the invention can be prepared by dry compressing powdery parahydroxybenzoic acid or its ester to give compressed material, pulverizing and classifying the material.

11 Claims, No Drawings

GRANULE OF PARAHYDROXYBENZOIC ACID OR PARAHYDROXYBENZOIC ESTER AND PROCESS FOR PRODUCING THE SAME

TECHNICAL FIELD

The present invention provides a granular product of parahydroxybenzoic acid or a parahydroxybenzoic acid ester having significantly suppressed dusting and caking tendency, and a process for preparing the same.

BACKGROUND ART

Parahydroxybenzoic acid can be employed as a monomer component for a wide variety of polymer products. Recently, it draws the attention of the art as a monomer component for preparing liquid crystalline polymers, which exhibit high strength and high elastic modulus. In addition, many of its alkyl esters have been employed as fungicide for cosmetic products or industrial purposes. Generally, parahydroxybenzoic acid is prepared by a method comprising the steps of reacting phenol with potassium hydroxide to give potassium phenoxide, reacting the obtained potassium phenoxide with carbon dioxide under pressure to give potassium parahydroxybenzoate and then, isolating the desired compound by means of acid precipitation, i.e. by adding a mineral acid to the salt.

For a long time, the Kolbe-Schmitt reaction, a solid-gas phase reaction, had been employed for the reaction of potassium phenoxide and carbon dioxide. Said reaction, however, has some problems such as long reaction time due to the solid-gas phase reaction, high amount waste of starting materials in side reaction because of thermal heterogeneity, difficulties in controlling the reaction which makes it difficult to attain a stable yield. In order to solve those problems, a number of methods had been proposed.

One of the instant inventors had proposed a process, which can produce the compound in a short time with high yield in a continuous manner. Said process comprises the step of reacting potassium phenoxide and carbon dioxide in the presence of an appropriate solvent at a temperature equal to or more than 180° C. in a dispersion, provided that phenol in an amount required to react with dipotassium parahydroxybenzoate to give potassium phenoxide is added to the reaction before the initiation of the carboxylation step (Japanese Patent Publication (KOKOKU) No. 9529/1970).

Thus obtained parahydroxybenzoic acid is then isolated from the solution by means of, such as, aciding out, filtration or centrifugation, and washed to give the compound to be used as a monomer component of polymers such as liquid crystalline polymers.

Parahydroxybenzoic acid esters may be prepared by a conventional process to obtain carboxylate esters; for example, by means of dehydration reaction between parahydroxybenzoic acid and an alcohol under the presence of acid catalyst such as sulfuric acid.

Crystalline product of parahydroxybenzoic acid or its ester usually comprises very fine particles and, therefore, is highly dusty causing operation problems. For example, when parahydroxybenzoic acid or its ester is added into a reaction vessel as a monomer component of a polymer or as a fungicide, fine particles of the compound fly in the air as powdery dust. The dust of parahydroxybenzoic acid or its ester flown in the air is hardly precipitated, and the widely dispersed dust causes problems in handling the same.

In order to diminish the problems concerning workability and safety in the feeding step, operators wear dust-proof glasses and masks and the reactor is mounted a vacuum at a position other than the supply port and a filter to trap the fine particles. However, they are not enough.

Upon storage, the fine particles of parahydroxybenzoic acid or its ester tend to form cake and the caking tendency also causes problems in handling the same. Since the specific surface area increase as the diameter of the fine particles decrease and parahydroxybenzoic acid or its ester is soluble to water, the fine particles apt to bridge each other due to moisture in the air to form cakes and the caking tendency may be augmented by the capillary phenomenon.

Further, the fine particles of parahydroxybenzoic acid or its ester are easily to be charged and therefore, adhere to the surfaces of containers or plastic bags because of the electrostatic action.

In order to suppress dust of the material with the above-described characteristics, granular product prepared by a wet extrusion granulating process comprising steps of adding water to the particles of parahydroxybenzoic acid or its ester, kneading and granulating the same by means of extrusion granulator and drying could be proposed. Although thus obtained granules exhibit somewhat suppressed dusting and electrostatic properties, the particles agglomerate more easily due to the added water and therefore, the problem of caking still remains. In addition, thus obtained granules are made of small particles which are attracted each other with relatively low bonding force, and tends to be degraded during transportation to give the original dusty small particles.

On the other hand, in the field of pharmaceutical preparation, it has been proposed that good granular product may be obtained by a method comprising the steps of adding binder component such as dextrin, starch and carboxymethyl cellulose as well as water or alcohol to the base component, kneading and granulating the same. However, adding a binder component during preparation of parahydroxybenzoic acid will deteriorate the purity of the product and polymer products or molded articles made from such a product might have imposed color tone or deteriorated properties.

DISCLOSURE OF THE INVENTION

Accordingly, the object of the present invention is to solve the above-mentioned problems and to provide granular product of parahydroxybenzoic acid or its ester with well-suppressed dusting and caking tendency.

The present invention provides a granular product of parahydroxybenzoic acid or its ester having an average particle size of equal to or more than 150 $\mu$m and a hardness of 10–3000 g.

The granular product of the present invention exhibits well suppressed dusting tendency and therefore, is easy to handle and affects little to environment and human beings. In addition the product exhibit suppressed caking tendency which also causes improved workability of the product. In addition, the granular product of parahydroxybenzoic acid or its ester is strong enough to resist against fairly strong impact such that it is not easily degraded to the original fine particles and therefore degradation of the product during transportation or the like is well suppressed.

The granular product of the present invention may be prepared by a method comprising the steps of, dry compressing powdery parahydroxybenzoic acid or its ester to give a compressed material, pulverizing and classifying the same. Accordingly, the method for preparing the granular product is also in the scope of the present invention.

DEFINITIONS

Average Particle Size

An average particle size represents the value measured as follows:

A sample product is weighted and then is sequentially screened with sieves having aperture of 2800 μm, 1700 μm, 1180 μm, 840 μm, 500 μm and 250 μm in this order. Firstly, the weighted sample product is screened with the sieve having aperture of 2800 μm at 230 rpm for 10 minutes. The amount of the residues on the sieve was weighted and the weight ratio (wt %) to the starting amount is calculated. The sample passed through the 2800 μm sieve was then screened with the sieve having aperture of 1700 μm in the same manner as above. These steps repeated successively and at the last, the amount of the product passed through the 250 μm sieve is weighed. The average particle size is the value calculated as follows: average particle size (μm)=(2800×residue on the 2800 μm sieve (wt %)/100)+(1700×residue on the 1700 μm sieve (wt %)/100)+(1180×residue on the 1180 μm sieve (wt %)/100)+(840×residue on the 840 μm sieve (wt %)/100)+(500×residue on the 500 μm sieve (wt %)/100)+(250×residue on the 250 μm sieve (wt %)/100)+(120×passed the 250 μm sieve (wt %)/100).

Hardness

Hardness is measured by the simplified granular hardness meter. The granular sample is applied load by means of a conical push-bar with 1 mmφ head and the weight at where the sample is disintegrated is taken for hardness of the sample.

Degradation Ratio Test Measured By Defacement Tester.

The degradation ratio test determines degradability of a granular product. Ten grams of the sample product is sieved with 60M-mesh screen (sieve having aperture of 0.25 mm) at 230 rpm for 1 minute. The residue on the sieve is loaded into defacement tester having inner diameter of 27 cm and thickness of 4 cm and is subjected to impact stress at 25 rpm for 3 minutes. Thus treated sample is sieved again with the 60M-mesh screen for 1 minute. The degradation ratio (%) is calculated with the amount of residue on the mesh before loading impact stress ($W_1$) and those after loading impact stress ($W_2$) according to the following formula:

$$\text{Degradation ratio }(\%) = (W_1 - W_2)/W_1 \times 100$$

Angle of repose, aerated bulk density and packed bulk density are determined by means of Powder Tester (Type PT-N), Hosokawa micron Co., according to the manufacture's instruction.

Angle of Repose

Sample is shaken on the standard sieve (10 mesh) to allow falling through a funnel and the angle of repose is measured by means of the pouring method.

Aerated Bulk Density

Sample is shaken on the sieve to allow falling into a standard container through the shout, and then the standard container is weighted to determine the aerated bulk density.

Packed Bulk Density

The sample is filled into a standard container, the container is tapped from a given height for given times and then, bulk density of the sample packed by tapping impact is determined.

Compression Ratio

The compression ratio is the value obtained according to the following formula:

$$(\text{packed bulk density} - \text{aerated bulk density})/\text{packed bulk density} \times 100$$

According to the present invention, the average particle size of the granular product of parahydroxybenzoic acid or its ester is equal to or more than 150 μm, preferably, 250–3000 μm, more preferably, 350–1600 μm. In case of the average particle size is less than 150 μm, satisfied dusting and caking suppression may not be achieved. In case of the average particle size is over 3000 μm, the product may exhibit well-suppressed dusting as well as caking tendency, but also low dissolution rate which may cause operation problems.

According to the present invention, the granular product of parahydroxybenzoic acid or its ester may contain less than 15 wt %, more preferably, less than 6 wt % of particles that pass through the 74 μm sieve. When the composition contains more than 15 wt % of the small particles that pass the 74 μm sieve, the product will dust extensively due to those small size particles.

According to the present invention, the hardness of the granular product of parahydroxybenzoic acid or its ester is 10–3000 g, and preferably, 10–1000 g. When the hardness is less than 10 g, the granular product may be easily degraded during transportation or the like into fine particles, which cause dusting. When the hardness is over 3000 g, the bonding force among the particles constituting the granule is too strong to be dissolved in a medium and may cause operation problems.

The granular product of parahydroxybenzoic acid or its ester may preferably be enough strong against impact or vibration stress such that it does not degrade easily into fine particles upon certain impact. Degradation ratio of the product measured by defacement tester, which is the index representing impact strength of the product, may be equal to or less than 3% such that the product is easy to handle in transporting and operating.

In addition, the angle of repose of the granular product of parahydroxybenzoic acid or its ester may be 30–50°, preferably, 35–45°. This range of the angle of repose demonstrates improved fluidity and therefore, improved handling property due to the larger particle size of the product.

The aerated bulk density of the granular product of parahydroxybenzoic acid or its ester may be 0.5–0.85 g/cc, preferably, 0.55–0.8 g/cc. The packed bulk density may be 0.55–0.9 g/cc and preferably, 0.6–0.85 g/cc.

Further, the compression ratio of the granular product of the present invention, which is the value obtained according to the following formula:

$$(\text{packed bulk density} - \text{aerated bulk density})/\text{packed bulk density} \times 100$$

may be equal to or less than 10%, preferably, equal to or less than 7%.

The compression ratio of the conventionally available powdery parahydroxybenzoic acid or its ester having a small particle size is as high as 30–60%; i.e. difference between the aerated bulk density and the packed bulk density is significant.

Accordingly, if the conventional powdery product of parahydroxybenzoic acid or its ester is packed in a standard container, there will be significant amount of air spaces between the particles.

To the contrary, the low compression ratio, as low as less than 10%, of the granular product of the present invention means the improved filling property, that is, the product filled even without tapping vibration or impact contains only small amount of air spaces.

According to the present invention, the granular product of parahydroxybenzoic acid or its ester may preferably be charged equal to or less than 0.02 µC/g. Due to the small amount of electrostatic charge, the problem of adhesion the product to the surfaces of containers or plastic-bags with electrostatic force is suppressed and therefore, the workability of the product can be substantially improved.

The granular product of parahydroxybenzoic acid or its ester of the present invention may be prepared by dry compressing powdery parahydroxybenzoic acid or its ester, pulverizing the compressed material and classifying the pulverized material. The starting material, parahydroxybenzoic acid or its ester may be any of those obtained by a conventional method. For example, alkaline metal salt of parahydroxybenzoic acid may be prepared according to the Kolbe-Schmidt reaction disclosed in Japanese Patent Publication (KOKOKU) No. 9529/1970, and then, parahydroxybenzoic acid may be obtained by aciding out the alkaline metal salt of parahydroxybenzoic acid at 80–100° C., and if desired, purifying. In such a method, the acid used in the aciding out step is not particularly limited, and an inorganic or organic acid may be used. Examples of inorganic acids include binary acid (hydrogen acid) such as hydrochloric acid and hydrofluoric acid, oxo acids such as nitric acid, sulfuric acid, phosphoric acid and perchloric acid. Examples of organic acids include fromic acid, acetic acid and phenol. The pH of the reaction in the aciding out step may be adjusted to 1–4 by means of the acid as above.

Parahydroxybenzoic acid esters may be prepared by a conventional method for preparing carboxylate esters. For example, the ester can be prepared by dehydration reaction between parahydroxybenzoic acid and an alcohol under the presence of an acid catalyst such as sulfuric acid.

Examples of parahydroxybenzoic acid esters preferably granulated according to the instant invention include alkyl esters having 1–4 carbon atoms such as methyl, ethyl, propyl, isopropyl, butyl and isobutyl ester and benzyl ester.

According to the present invention, thus obtained powdery parahydroxybenzoic acid or its ester is dry compressed, the compressed material is then pulverized and classified to give the granular product of the present invention.

Generally, the term "granulating" or "granulation" represents a process to provide granular product consisting of particles each having almost same size and shape, from a starting material in the form of powder, melt or aqueous solution. There are many known granulation processes such as extrusion, spray drying, milling, mixing and fluidized bed granulation. In the process of the present invention, the powdery parahydroxybenzoic acid or its ester is dry compressed with a compressor to give compressed material, the compressed material is then pulverized and classified to give granular product of the present invention. This type of procedure is generally called as dry milling granulation.

The dry compressing step may be carried out mechanically under compression pressure of 0.2–2.0 ton/cm. When the compression pressure is less than 0.2 ton/cm, the bonding force among the fine particles constituting the resulting granule becomes weak and the granule may easily be degraded. When the pressure is over 2.0 ton/cm, the bonding force becomes too strong and the solubility of the granule, which can be used as fungicide for cosmetic products or industrial purposes, to alcohol or the like is spoiled. The roll used in the dry compressing step may preferably be corrugated roll or smooth slit roll.

The compressed material obtained by mechanical compression is then pulverized by means of a mill and then classified to give granular product of parahydroxybenzoic acid or its ester with certain particle characteristics. The mill used in this step may be, for example, roll mill, medium mill, gas flow mill, shearing and grinding mill, and the like, and hammer type high speed rotary impact mill is preferably used.

The pulverized granules are then classified. The classifying step may generally be carried out according to a known process, for example, by means of a mesh screen of suitable size. The smaller particles removed by the classifying step may be returned to the compressing step, and the larger particles may be returned to the pulverizing step. Accordingly, the present process can prepare granular parahydroxybenzoic acid and its ester with an excellent yield.

According to the present invention, due to the high pressure in the granulating process, the primary particles constituting the granule firmly agglomerate such that the particles are attracted by van der Waals force and electrostatic forces each other. This situation is different from those obtained by conventional wet extrusion granulation wherein the primary particles constituting the granule are associated due to surface tension of the binder component. Therefore, the granular product of parahydroxybenzoic acid or its ester obtained according to the present invention is strong enough to resist against impact stress and can be dissolved in a medium quite easily, and therefore, is excellent in operability.

According to the present invention, the parahydroxybenzoic acid or its ester having a small average particle size used as starting material may be any of those prepared by a conventional method and employed without adjusting water content. Accordingly, the step adding water to the starting powdery material, which was essential for the conventional wet extrusion granulation process, is no longer required and therefore, the process of the present invention is suitable for large scale production.

In the present specification, the term "dry compressing" represents the step to compress the material without adding any binder component such as water, and does not mean that the starting material does not contain water at all. It is preferable that water content of the starting material, powdery parahydroxybenzoic acid or its ester is less than 20%, more preferably less than 12%, especially less than 6%. By dry compressing of powdery parahydroxybenzoic acid or its ester containing only small amount of water, granular product with high impact strength and good solubility described as above can be obtained.

The granular product of parahydroxybenzoic acid or its ester of the present invention may be employed as a monomer for preparing polymer materials or as a fungicide for cosmetic products or industrial purposes.

The present invention is further illustrated by means of the attached examples.

EXAMPLE 1

Powdery parahydroxybenzoic acid having a small particle size (approx. 40–70 µm; water content: 0.1%) prepared by the conventional Kolbe-Schmitt reaction was subjected to mechanical compression with compression granulator BRIKETTA BCS-IV (SINTOKOGIO,LTD) under the conditions shown in table 1 to provide compressed material. The compressing pressure was controlled by adjusting roll speed and feeding speed of powdery parahydroxybenzoic acid to the rolls (adjusted by screw speed) over the constant diameter of the rolls and distance between the rolls.

Thus obtained compressed material was then pulverized by means of hammer type high speed rotating impact mill (SINTOKOGIO,LTD) and classified with a series of mesh screens to provide granular product of parahydroxybenzoic acid having particle properties shown in table 2 (samples 1-1–1-7).

EXAMPLE 2

Powdery butyl parahydroxybenzoate having a small particle size (approx. 40–70 µm; water content: 0.05%) prepared by a conventional reaction was subjected to mechanical compression in the same manner as example 1 under the condition shown in table 1 to give compressed material. The compressed material was pulverized and classified in the same manner as example 1 to provide granular product of butyl parahydroxybenzoate having particle properties shown in table 3 (samples 2-1–2-7).

EXAMPLE 3

Powdery propyl parahydroxybenzoate having a small particle size (approx. 40–70 µm; water content: 0.05%) prepared by a conventional reaction was subjected to mechanical compression in the same manner as example 1 under the condition shown in table 1 to give compressed material. The compressed material was pulverized and classified in the same manner as example 1 to provide granular product of propyl parahydroxybenzoate having particle properties shown in table 4 (samples 3-1–3-7).

EXAMPLE 4

Powdery ethyl parahydroxybenzoate having a small particle size (approx. 40–70 µm; water content: 0.05%) prepared by a conventional reaction was subjected to mechanical compression in the same manner as example 1 under the condition shown in table 1 to give compressed material. The compressed material was pulverized and classified in the same manner as example 1 to provide granular product of ethyl parahydroxybenzoate having particle properties shown in table 5 (samples 4-1–4-7).

EXAMPLE 5

Powdery methyl parahydroxybenzoate having a small particle size (approx. 40–70 µm; water content: 0.05%) prepared by a conventional reaction was subjected to mechanical compression in the same manner as example 1 under the condition shown in table 1 to give compressed material. The compressed material was pulverized and classified in the same manner as example 1 to provide granular product of methyl parahydroxybenzoate having particle properties shown in table 6 (samples 5-1–5-7).

The compressing conditions in the Examples 1–5 are as follows:

TABLE 1

| | Compressing Conditions | | | |
|---|---|---|---|---|
| Example No. | Type of roll | roll speed (rpm) | screw speed (rpm) | pressure (ton/cm) |
| Example 1 | Smooth slit | 14 | 70 | 0.79 |
| Example 2 | Smooth slit | 14 | 70 | 0.30 |
| Example 3 | Smooth slit | 12 | 70 | 1.05 |
| Example 4 | Smooth slit | 12 | 70 | 0.35 |
| Example 5 | Smooth slit | 20 | 30 | 1.09 |

Particle characteristics of the granular products of examples 1–5 are shown in tables 2–6 and the hardness, degradation ratio and dusting tendency are shown in table 7.

TABLE 2

| | | particle characteristics | | | | | | | |
|---|---|---|---|---|---|---|---|---|---|
| | average | | particle distribution | | | | | | |
| sample No. | particle size (µm) | more than 2800 | 1700~ 2800 | 1180~ 1700 | 840~ 1180 | 500~ 840 | 250~ 500 | less than 250 | less than 74 |
| 1-1 | 2708 | 93.2 | 5.1 | 0.5 | 0.4 | 0.3 | 0.3 | 0.2 | 0.0 |
| 1-2 | 1561 | 0.0 | 77.0 | 20.4 | 0.6 | 0.7 | 0.9 | 0.5 | 0.3 |
| 1-3 | 1137 | 0.0 | 0.3 | 92.1 | 4.8 | 0.3 | 0.4 | 2.2 | 1.2 |
| 1-4 | 811 | 0.0 | 0.3 | 1.5 | 90.3 | 5.1 | 0.8 | 2.0 | 1.0 |
| 1-5 | 487 | 0.0 | 0.3 | 0.4 | 1.0 | 90.5 | 5.6 | 2.2 | 1.4 |
| 1-6 | 240 | 0.0 | 0.3 | 0.4 | 0.3 | 0.2 | 82.4 | 16.4 | 8.8 |
| 1-7 | 129 | 0.0 | 0.0 | 0.1 | 0.2 | 0.4 | 0.5 | 98.9 | 46.7 |

TABLE 3

| | | particle characteristics | | | | | | | |
|---|---|---|---|---|---|---|---|---|---|
| | average | | particle distribution | | | | | | |
| sample No. | particle size (µm) | more than 2800 | 1700~ 2800 | 1180~ 1700 | 840~ 1180 | 500~ 840 | 250~ 500 | less than 250 | less than 74 |
| 2-1 | 2692 | 92.7 | 4.3 | 1.2 | 0.6 | 0.5 | 0.3 | 0.4 | 0.2 |
| 2-2 | 1623 | 0.0 | 88.9 | 7.5 | 1.5 | 0.3 | 0.3 | 1.3 | 1.3 |
| 2-3 | 1223 | 0.0 | 12.4 | 83.1 | 3.0 | 1.0 | 0.5 | 0.0 | 0.0 |
| 2-4 | 821 | 0.0 | 0.0 | 1.4 | 92.3 | 5.5 | 0.9 | 0.0 | 0.0 |
| 2-5 | 497 | 0.0 | 0.0 | 0.1 | 2.1 | 93.8 | 3.5 | 0.5 | 0.5 |
| 2-6 | 256 | 0.0 | 0.0 | 0.0 | 1.1 | 1.0 | 95.4 | 2.5 | 2.5 |
| 2-7 | 123 | 0.0 | 0.0 | 0.0 | 0.1 | 0.5 | 0.4 | 99.0 | 45.7 |

TABLE 4

| | | particle characteristics | | | | | | | |
| | average | | particle distribution (%) | | | | | | |
| sample No. | particle size (μm) | more than 2800 | 1700~ 2800 | 1180~ 1700 | 840~ 1180 | 500~ 840 | 250~ 500 | less than 250 | less than 74 |
|---|---|---|---|---|---|---|---|---|---|
| 3-1 | 2723 | 94.2 | 4.7 | 0.2 | 0.2 | 0.1 | 0.2 | 0.4 | 0.3 |
| 3-2 | 1613 | 0.0 | 87.1 | 9.3 | 2.0 | 0.8 | 0.7 | 0.1 | 0.0 |
| 3-3 | 1125 | 0.0 | 0.9 | 87.6 | 7.4 | 2.0 | 1.2 | 0.9 | 0.2 |
| 3-4 | 799 | 0.0 | 0.0 | 1.2 | 88.0 | 7.8 | 1.9 | 1.1 | 0.6 |
| 3-5 | 482 | 0.0 | 0.0 | 0.5 | 1.7 | 88.0 | 7.9 | 1.9 | 0.7 |
| 3-6 | 253 | 0.0 | 0.1 | 0.2 | 0.9 | 0.6 | 89.5 | 8.7 | 3.3 |
| 3-7 | 125 | 0.0 | 0.0 | 0.1 | 0.3 | 0.3 | 0.6 | 98.8 | 41.8 |

TABLE 5

| | | particle characteristics | | | | | | | |
| | average | | particle distribution (%) | | | | | | |
| sample No. | particle size (μm) | more than 2800 | 1700~ 2800 | 1180~ 1700 | 840~ 1180 | 500~ 840 | 250~ 500 | less than 250 | less than 74 |
|---|---|---|---|---|---|---|---|---|---|
| 4-1 | 2730 | 94.7 | 4.2 | 0.3 | 0.2 | 0.2 | 0.2 | 0.2 | 0.1 |
| 4-2 | 1556 | 0.0 | 81.5 | 11.6 | 2.7 | 1.2 | 1.8 | 1.2 | 0.4 |
| 4-3 | 1107 | 0.0 | 0.8 | 83.1 | 11.3 | 2.6 | 1.4 | 0.8 | 0.3 |
| 4-4 | 782 | 0.0 | 0.2 | 0.5 | 84.4 | 11.5 | 2.2 | 1.3 | 0.4 |
| 4-5 | 482 | 0.0 | 0.0 | 0.0 | 1.5 | 90.2 | 6.8 | 1.5 | 0.6 |
| 4-6 | 253 | 0.0 | 0.3 | 0.2 | 0.9 | 0.6 | 90.7 | 7.3 | 3.8 |
| 4-7 | 127 | 0.0 | 0.1 | 0.1 | 0.4 | 0.3 | 0.5 | 98.6 | 42.3 |

TABLE 6

| | | particle characteristics | | | | | | | |
| | average | | particle distribution (%) | | | | | | |
| sample No. | particle size (μm) | more than 2800 | 1700~ 2800 | 1180~ 1700 | 840~ 1180 | 500~ 840 | 250~ 500 | less than 250 | less than 74 |
|---|---|---|---|---|---|---|---|---|---|
| 5-1 | 2736 | 95.2 | 3.7 | 0.4 | 0.1 | 0.2 | 0.3 | 0.1 | 0.0 |
| 5-2 | 1655 | 1.0 | 91.8 | 4.5 | 0.9 | 0.4 | 0.4 | 0.8 | 0.3 |
| 5-3 | 1130 | 0.0 | 0.7 | 88.6 | 7.6 | 1.3 | 1.1 | 0.8 | 0.4 |
| 5-4 | 783 | 0.0 | 0.3 | 0.7 | 84.7 | 9.7 | 3.0 | 1.7 | 1.0 |
| 5-5 | 471 | 0.0 | 0.0 | 0.0 | 2.7 | 83.7 | 10.4 | 3.2 | 1.5 |
| 5-6 | 268 | 0.0 | 0.3 | 0.3 | 3.1 | 1.4 | 85.4 | 9.4 | 3.6 |
| 5-7 | 126 | 0.0 | 0.0 | 0.2 | 0.3 | 0.2 | 0.6 | 98.7 | 48.7 |

TABLE 7

| sample No. | hardness (g) | degradation ratio (%) | dust distribution (cm) | |
| | | | distance | height |
|---|---|---|---|---|
| 1-1 | 187 | 0.95 | 30 | 25 |
| 1-2 | 104 | 1.03 | 30 | 25 |
| 1-3 | 98 | 0.85 | 35 | 20 |
| 1-4 | 45 | 0.87 | 40 | 25 |
| 1-5 | 15 | 0.96 | 35 | 25 |
| 1-6 | — | — | 40 | 30 |
| 1-7 | — | — | 70 | over |
| 2-1 | 164 | 1.13 | 35 | 25 |
| 2-2 | 125 | 1.25 | 30 | 20 |
| 2-3 | 100 | 0.98 | 30 | 25 |
| 2-4 | 50 | 1.03 | 35 | 30 |
| 2-5 | 20 | 1.28 | 40 | 30 |
| 2-6 | — | — | 35 | 45 |
| 2-7 | — | — | 70 | over |
| 3-1 | 274 | 0.85 | 30 | 25 |
| 3-2 | 143 | 0.78 | 35 | 25 |
| 3-3 | 46 | 0.99 | 30 | 20 |
| 3-4 | 43 | 1.04 | 30 | 30 |
| 3-5 | 15 | 1.00 | 40 | 30 |
| 3-6 | — | — | 45 | 35 |
| 3-7 | — | — | over | over |
| 4-1 | 102 | 0.89 | 30 | 30 |
| 4-2 | 144 | 0.94 | 30 | 25 |
| 4-3 | 66 | 0.86 | 35 | 35 |

TABLE 7-continued

| sample No. | hardness (g) | degradation ratio (%) | dust distribution (cm) | |
|---|---|---|---|---|
| | | | distance | height |
| 4-4 | 38 | 1.02 | 35 | 30 |
| 4-5 | 11 | 0.84 | 45 | 30 |
| 4-6 | — | — | 45 | 35 |
| 4-7 | — | — | over | over |
| 5-1 | 274 | 1.12 | 25 | 25 |
| 5-2 | 143 | 0.87 | 25 | 30 |
| 5-3 | 46 | 0.98 | 30 | 25 |
| 5-4 | 43 | 1.01 | 35 | 30 |
| 5-5 | 15 | 1.06 | 45 | 35 |
| 5-6 | — | — | 45 | 35 |
| 5-7 | — | — | 70 | over |

The average particle size shown in tables 2–6 was determined by screening the sample with the sieves described as above using a shaker (Iida Seisaku Sho ES-65), and weighting the residues on the respective sieves and those passed the sieves. The average particle size was determined according to the formula described in the DEFINITIONS as above. Particles, which passed the 250 μm-sieve were further sieved with the 74 μm-sieve and the amount passed the 74 μm-sieve was weighed and the ratio of the same were calculated.

In addition to the above, hardness, degradation ratio, and dust distribution shown in table 7 were obtained as follows:

Hardness

Hardness was measured by means of simplified hardness meter (TSUTSUI RIKAGAKU KIKAI CO.,LTD.) as follows. Firstly, the pointer of the hardness meter was confirmed to be at the position 0. The sample (i.e. granulated product of parahydroxybenzoic acid) was put on the sample stage with a tweezers and the head of the push bar was contacted to the center of the sample granule. Then, weight was loaded by operating handle of the hardness meter and the value at which the granule was disintegrated was recorded. The value was determined 10 or more times per one sample and the average was calculated.

Hardness of the sample granules having less than 0.3 mm particle size could not be measured because it was difficult to put the same at the correct location.

Degradation Ratio

Degradation ratio was determined by means of deface-ment tester (KAYAGAKI IRIKA KOGYO, LTD.) as follows. Ten (10) grams of the sample was weighed and sieved with 60M-mesh screen (sieve having aperture of 0.25 mm) for 1 minute by means of the same shaker used for particle size determination (Iida Seisakusyo, ES-65). The residue on the sieve was loaded into the defacement tester having inner diameter of 27 cm and thickness of 4 cm and was subjected to impact stress at 25 rpm for 3 minutes. After that, the resulting samples were sieved again with the 60M-mesh screen for 1 minute. The degradation ratio (%) was calculated from the amount of residue on the mesh before impact stress ($W_1$) and those after impact stress ($W_2$) according to the following formula:

$$\text{Degradation ratio } (\%) = (W_1 - W_2)/W_1 \times 100$$

The granular products having a particle size of less than 0.3 mm were qualified as those already degraded and were not subjected to this evaluation.

Dust Dispersion

Dust dispersion tester was used for this evaluation. 50 g of the granular sample was slid down along the slope of 60° for 50 cm. When the composition reached to the bottom of the slope, the height and distance to which the dust flew were measured. When the distance was over 70 cm and height was over 50 cm, they were qualified as "over".

The samples prepared by dry compressing as disclosed in the examples 1–5 which had an average diameter of more than 150 μm and a hardness of more than 70 g (Sample Nos. 1-1–1-5, Nos. 2-1–2-5, Nos. 3-1–3-5, Nos. 4-1–4-5 and Nos. 5-1–5-5). These samples were shown to be strong enough to resist against impact stress based on less than 3% of degradation ration. Further, the samples were shown to attain a good operability based on less than 50 cm in distance of dust distribution.

To the contrarily, samples having less than 150 μm of average diameter (Nos. 1-7, 2-7, 3-7, 4-7 and 5-7) had problems in operability because of more than 50 cm in distance of dust distribution.

EXAMPLE 6

Samples prepared in examples 1–5 were combined according to the following so that the obtained composition can imitate actual products to give samples Nos. 1-8–5-8.

Sample 1-8: No. 1-2(4.01%), No. 1-3(43.05%), No. 1-4 (28.06%), No. 1-5(24.88%)

Sample 2-8: No. 2-2(31.76%), No. 2-3(32.94%), No. 2-4(21.05%), No. 2-5(14.25%)

Sample 3-8: No. 3-2(17.55%), No. 3-3(30.98%), No. 3-4(25.08%), No. 3-5(26.39%)

Sample 4-8: No. 4-2(7.19%), No. 4-3(22.62%), No. 4-4 (30.87%), No. 4-5(39.32%)

Sample 5-8: No. 5-2(49.15%), No. 5-3(25.55%), No. 5-4(14.00%), No. 5-5(11.30%)

In addition to the above, the respective starting materials of which average particle sizes are within the range of 40–70 μm were subjected to the evaluation as sample 1-9–5-9:

Sample 1-9: untreated powdery parahydroxybenzoic acid.

Sample 2-9: untreated powdery butyl parahydroxybenzoate.

Sample 3-9: untreated powdery propyl parahydroxybenzoate.

sample 4-9: untreated powdery ethyl parahydroxybenzoate.

Sample 5-9: untreated powdery methyl parahydroxybenzoate.

With respect these samples, particle characteristics are shown in Table 8 and caking properties are shown in table 9.

TABLE 8

| | particle characteristics | | | | | | |
|---|---|---|---|---|---|---|---|
| Sample No. | angle of repose (deg.) | spatula angle (deg.) | bulk density (g/cc) | | compression ratio (%) | distance (cm) | height (cm) |
| | | | aerated | packed | | | |
| 1-8 | 40.3 | 46.5 | 0.772 | 0.797 | 3.1 | 50 | 20 |
| 2-8 | 41.1 | 41.8 | 0.593 | 0.630 | 5.9 | 40 | 30 |
| 3-8 | 43.2 | 43.7 | 0.613 | 0.643 | 4.7 | 40 | 30 |
| 4-8 | 42.8 | 45.7 | 0.628 | 0.645 | 3.6 | 40 | 20 |
| 5-8 | 42.6 | 44.1 | 0.629 | 0.661 | 4.8 | 50 | 30 |
| 1-9 | 51.5 | 66.5 | 0.582 | 0.829 | 29.8 | over | over |
| 2-9 | 55.8 | 70.4 | 0.327 | 0.678 | 51.8 | over | over |

TABLE 8-continued particle characteristics

| Sample No. | angle of repose (deg.) | spatula angle (deg.) | bulk density (g/cc) aerated | bulk density (g/cc) packed | compression ratio (%) | distance (cm) | height (cm) |
|---|---|---|---|---|---|---|---|
| 3-9 | 58.3 | 63.9 | 0.365 | 0.857 | 57.4 | over | over |
| 4-9 | 57.6 | 54.6 | 0.372 | 0.645 | 42.3 | over | over |
| 5-9 | 61.9 | 58.6 | 0.278 | 0.626 | 55.6 | over | over |

TABLE 9

Caking tendency

| Sample No. | disintegration weight (g) |
|---|---|
| 1-8 | 0 |
| 2-8 | 50 |
| 1-9 | 400 |
| 2-9 | 1000 |

Particle characteristics including angle of repose, spatula angle and relative density were determined. The measurement was carried out with Powder Tester (Type PT-N, Hosokawa micron Co.) according to the manufacturer's instruction. Spatula angle was determined as the angle of the composition deposited on the spatula.

Caking Tendency

Thirty (30) grams of the sample was filled in a glass tube of internal diameter 40 mm and height 60 mm. On the upper surface of the sample, cardboard disk, glass plate, silicone plug and 500 g weight were put in this order and the tube was allowed to stand for 3 days at room temperature. After that, the sample was removed from the tube and then, weights were loaded accumulatively on the sample cake until the cake was disintegrated. The amount of the weights at the time of disintegration was determined as disintegration weight. As the disintegration weight decreases, the caking tendency is evaluated as lower.

Sample Nos. 1-8, 2-8, 3-8, 4-8 and 5-8 of Example 6 were prepared by combining the samples obtained in examples 1–5 so that the composition can imitate actual products. Both of the angle of repose and spatula angle were small, showing that fluidity of these samples were improved than those untreated fine particles of parahydroxybenzoic acid or its ester (sample Nos. 1-9, 2-9, 3-9, 4-9 and 5-9). The compression ratios of these samples were less than 7%, showing good filling ability. Further, the small dust dispersion distance of the samples meant that the granular products were excellent in workability. Further more, caking of the sample Nos. 1-8 and 2-8 during storage were significantly prevented (disintegration weight 0 means caking of the samples were not occurred) also demonstrated that the granular products were excellent in workability.

INDUSTRIAL APPLICABILITY

Parahydroxybenzoic acid may be used as a monomer component for preparing wide variety of polymer materials and especially, it draws the attention of the art as a monomer component for preparing liquid crystalline polymers, which exhibit high strength and high elastic modulus. In addition, many of its alkyl esters have been employed as fungicide for cosmetic products or industrial purposes. The granular product of parahydroxybenzoic acid or its ester of the instant invention exhibit well suppressed dusting tendency and therefore, is easy to handle and affects little to environment and human beings. In addition the product hardly be caked at storage which also improve workability of the product. Further, the granular product of parahydroxybenzoic acid or its ester is strong enough to resist against fairly strong impact such that it is not degraded into the original fine particles by certain impact. Therefore the products of the invention are easy for handling upon transportation.

What is claimed is:

1. A granular product of parahydroxybenzoic acid or its ester, characterized in that having an average particle size of equal to or more than 150 μm and a hardness of 10–3000 g.

2. The granular product according to claim 1, characterized in that the proportion of the particles which pass through a sieve with 74 μm of aperture to whole product is equal to or less than 15 wt %.

3. The granular product according to claim 1, characterized in that the degradation ratio is equal to or less than 3%.

4. The granular product according to claim 1, characterized in that the angle of repose is 30–50°.

5. The granular product according to claim 1, characterized in that the aerated bulk density is 0.5–0.85 g/cc, packed bulk density is 0.55–0.9 g/cc and compression ratio calculated as below:

(packed bulk density−aerated bulk density)/packed bulk density× 100 is equal to or less than 10%.

6. The granular product of according to claim 1, which is prepared by the process comprising the steps of dry compressing powdery parahydroxybenzoic acid or its ester to give compressed material, pulverizing the compressed material and classifying.

7. The granular product according to claim 6, wherein the dry compressing is carried out under the pressure of 0.2–2.0 ton/cm.

8. The granular product according to claim 6, wherein the water content of the powdery parahydroxybenzoic acid or its ester is equal to or less than 20%.

9. A process for preparing the granular product of parahydroxybenzoic acid or its ester of claim 1, comprising the steps of dry compressing powdery parahydroxybenzoic acid or its ester to give compressed material, pulverizing the compressed material to give granules and classifying.

10. The process of claim 9, wherein the dry compressing step is carried out at the pressure of 0.2–2.0 ton/cm.

11. The process of claim 9, wherein the water content of the powdery parahydroxybenzoic acid or its ester is equal to or less than 20%.

* * * * *